United States Patent [19]

Young

[11] Patent Number: 5,266,493
[45] Date of Patent: Nov. 30, 1993

[54] MONITORING BORIC ACID IN FLUID SYSTEMS

[75] Inventor: Paul R. Young, Wheaton, Ill.

[73] Assignee: Nalco Chemical Company, Naperville, Ill.

[21] Appl. No.: 8,702

[22] Filed: Jan. 22, 1993

[51] Int. Cl.$^5$ ...................... G01N 35/08; G01N 37/00
[52] U.S. Cl. ........................................ 436/55; 436/56; 422/3; 422/14; 422/62; 210/696; 210/699; 210/701
[58] Field of Search ....................... 210/701, 696, 699; 436/55, 56; 422/62, 3, 14

[56] References Cited

U.S. PATENT DOCUMENTS

| | | | |
|---|---|---|---|
| 4,472,354 | 9/1984 | Passell et al. | 422/62 |
| 4,532,047 | 7/1985 | Dubin | 210/698 |
| 4,584,104 | 4/1986 | Dubin | 210/696 |
| 4,783,314 | 11/1988 | Hoots et al. | 422/3 |
| 4,950,463 | 8/1990 | Murray | 422/3 |
| 4,966,711 | 10/1990 | Hoots et al. | 210/697 |
| 4,992,380 | 2/1991 | Moriarty et al. | 436/55 |
| 5,006,311 | 4/1991 | Hoots et al. | 422/62 |
| 5,041,386 | 8/1991 | Pierce et al. | 436/50 |
| 5,128,419 | 7/1992 | Fong et al. | 525/351 |
| 5,171,450 | 12/1992 | Hoots | 210/701 |
| 5,200,106 | 4/1993 | Hoots et al. | 252/181 |

FOREIGN PATENT DOCUMENTS 0062306 10/1982 European Pat. Off. .
2657851 6/1978 Fed. Rep. of Germany .
2238383 5/1991 United Kingdom .

OTHER PUBLICATIONS

"Practical Applications of Tracers-Beyond Product Monitoring", J. E. Hoots, Cooling Tower Institute 1990 Annual Meeting, Technical Paper Number TP90-01, 14 pp, presented Feb. 1990.

"Effluent monitoring For Oil in Water", K. Coursin, Pollution Engineering, pp. 100-102 Nov. 1988.

"Use of Fluorescence Spectroscopy for Monitoring Petroleum Hydrocarbon Contamination in Estuarine and Ocean Waters", W. A. Maher, Bull. Environ. Contam. Toxicol, 30, pp. 413-419, 1983.

"Fluorescence Cell Design and Use to Determine Crude Oil in Water", P. John, E. R. McQuat and I. Soutar, Analyst (London), vol. 107, pp. 221-223, Feb., 1982.

"Spectroscopic Techniques for Quality Assurance of Oil Field Corrosion Inhibitors", J. A. Martin pp. 465-473, presented Corrosion/84, Paper No. 223, Apr. 1984, New Orleans, La.

"The Existence of Imidazoline Corrosion Inhibitors", J. A. Martin and F. W. Valone, National Association of Corrosion Engineers, May 1985, vol. 41, No. 5, pp. 281-287 presented Corrosion/84, paper No. 232, Apr., 1984, New Orleans, La.

Literature Search Report No. 4118, Apr. 13, 1992, subject entitled "Use of Natural Fluorescence to Detect Process Leaks Into Water Systems, Especially Cooling Towers", pp. 1-24.

Literature Search Report No. 3244, Jul. 19, 1990, subject entitled "Continuous On-line Fluorescence Monitoring of Soluble Oils In Water, Wasterwater Or Other Aqueous Solutions", pp. 1-26 plus 7 additional pages.

"Use of Fluorescent Tracers to monitor Internal Boiler Treatments and to Determine Boiler Operating Parameters", R. W. Fowee and C. C. Pierce, Nalco Chemical Company, 10 pp, presented at the National Association of Corrosion Engineers Corrosion '90 meeting, Las Vegas, Nev., Apr. 23-27, 1990.

Literature Search Report No. 4294, Sep. 29, 1992, subject entitled "Patent Extensions of Trasar Technology: Uses of Tracers", pp. 1-64.

Primary Examiner—James C. Housel
Assistant Examiner—N. Bhat
Attorney, Agent, or Firm—Joan I. Norek; Robert A. Miller; Joseph B. Barrett

[57] ABSTRACT

A process monitors boric acid or other boron compounds in a fluid system. At least one specie of tracer chemical is added to a fluid system and at least one sample of fluid from the fluid system is analyzed for at least the presence of the tracer, and the presence of the specie of tracer chemical in such sample determines at least the presence of boric acid or other boron compounds in the sample.

20 Claims, No Drawings

MONITORING BORIC ACID IN FLUID SYSTEMS

TECHNICAL FIELD OF THE INVENTION

The present invention is in the technical field of monitoring boric acid compositions, such as silica scale inhibitor compositions containing boric acid, monitoring water treatment processes using boric acid, and boric acid water treatment processes.

BACKGROUND OF THE INVENTION

Boric acid is used commercially as a water treatment agent, particularly as an agent that inhibits the formation of amorphous silica scale in industrial water systems. The use of an admixture of a water-soluble polypolar organic compound containing hydroxyl, primary amino, or secondary amino functional groups, and having a molecular weight not exceeding 500, together with boric acid or another boron compound that forms orthoborate ion when dissolved in or hydrolyzed by water, as an inhibitor of amorphous silica scale formation on surfaces in contact with industrial waters, is taught in U.S. Pat. No. 4,532,047, issued on Jul. 30, 1985, inventor Leonard Dubin, incorporated hereinto by reference. Also disclosed in this patent is that boric acid and its water-soluble salts and/or any boron compound that forms orthoborate ion by dissolving in industrial waters or by hydrolysis under industrial water environments may by themselves protect against and inhibit the formation of amorphous silica scale on surfaces in contact with these industrial waters. The use of boric acid and/or such other boron compounds by themselves as amorphous silica scale inhibitor agents is also disclosed, and is described in more detail, in U.S. Pat. No. 4,584,104, issued Apr. 22, 1986, inventor Leonard Dubin, incorporated hereinto by reference.

Boric acid also has other commercial and/or industrial applications. Boric acid is commonly added to commercial plating solutions as a buffer. Boric acid, which has bacteriostatic and fungicidal properties, is used in washing citric fruits to inhibit mold, as an additive to mildew-resistant latex paints, and as a mild antiseptic additive in consumer products such as mouthwashes, hair rinses, and the like. Boron compounds are good absorbers of thermal neutrons, and thus are found in many nuclear industry applications. For instance, high purity boric acid is added to the cooling water used in high-pressure water reactors. Boric acid is also used as a fire retardant.

In the aforementioned commercial and/or industrial uses of boric acid, which generally are also applicable to its water-soluble salts and/or any boron compound that forms orthoborate ion by dissolving in water or by hydrolysis under water environments, the boron compound is or may be employed as a solute in an aqueous system. When boric acid and/or its water-soluble salts and/or any boron compound that forms orthoborate ion by dissolving in water or by hydrolysis under water environments, is so employed as a solute in an aqueous system, it often is desirable to monitor the boric acid and/or its water-soluble salts and/or any boron compound that forms orthoborate ion by dissolving in water or by hydrolysis under water environments (referred to at times hereinafter as "boron compound(s)"), in such system. By the terminology of "monitor" and/or "monitoring" is meant herein, unless expressly stated otherwise, the tracing or tracking to determine the location and/or route of such boron compound(s) in the aqueous system or loss of such boron compound(s) from the aqueous system, and/or the determination of the concentration or amount of the boron compound(s) at any given site or within any given area, including singular, intermittent semi-continuous monitoring. The test methods most commonly used presently to determine the presence and/or concentration of boric acid in aqueous systems are difficult to perform or not very accurate. One such method, known in the technical field as the carmine red method, is hazardous to perform because it requires the use of concentrated acid. Methods which measure color development with a comparator are less accurate than desired, for instance not distinguishing between a boric acid concentration of 70 ppm and 100 ppm. Another method, known in the technical field as the mannital titration method, can suffer from interferences. It is an object of the present invention to provide an improved process for monitoring a boron compound composition, in a fluid system, particularly an aqueous system, and more particularly when such composition is fed to the fluid system as a silica scale deposit inhibitor. It is an object of the present invention to provide an improved process for the treatment of an industrial water system (aqueous industrial system) in which a boron compound(s) is an active treatment agent, the improvement characterized by feeding to such water system a composition, particularly a solution such as an aqueous-based solution, containing a boron compound(s) and having enhanced detectability. It is an object of the present invention to provide an improved process for the treatment of an industrial water system in which a boron compound(s) is an active treatment agent, the improvement characterized by feeding to such water system an aqueous-based boron compound(s) composition having such enhanced detectability that the monitoring of the boron compound(s) requires no hazardous materials, and is very sensitive and accurate. These and other objects of the present invention are described in more detail below.

DISCLOSURE OF THE INVENTION

The present invention provides a method or process for monitoring boric acid and its water-soluble salts, and/or any boron compound that forms orthoborate ion by dissolving in water or by hydrolysis under water environments, in a fluid system comprising feeding to such fluid system a substantially homogeneous admixture of such a boron compound(s) and at least one signature chemical, and thereafter subjecting at least a sample of such fluid system to analysis to detect the presence and/or the concentration of such signature chemical, and at times the concentration change and/or concentration gradient of the signature compound in such fluid system. In a preferred embodiment such fluid system is an aqueous-based fluid system. In another preferred embodiment the signature chemical is a fluorescent compound and the analysis is a fluorescence analysis or a combination of high pressure liquid chromatography and fluorescence analysis. In another preferred embodiment the signature chemical is a transition metal and the analysis is a transition metal-responsive analysis, or a combination of high pressure liquid chromatography and a transition metal-responsive analysis. In these embodiments and in other preferred embodiments, described in detail below, the boron compound(s) is preferably fed to the fluid system as an aqueous boron compound(s) solution (liquid boron compound(s) composition) or as a concentrated liquid boron compound(s) composition that includes a water-soluble polypolar organic compound containing hydroxyl, primary amino, or secondary amino functional groups, and having a molecular weight not exceeding 500, preferably a (poly)ethanol amine. The present invention also provides an aqueous-based boron compound(s) composition which further includes a signature chemical, particularly a signature chemical that may be detected as to its presence and/or concentration by fluorescence analysis, a combination of high pressure liquid chromatography and fluorescence analysis, transition metal-responsive analysis, or a combination of high pressure liquid chromatography and a transition metal-responsive analysis. In preferred embodiment such an aqueous-based boron compound(s) composition is one having enhanced boron compound(s) solubility comprised of (poly)ethanol amine, boron compound(s), particularly boric acid, and water. The present invention also provides an improved process for the treatment of an industrial water system (aqueous industrial system) wherein a boron compound(s) is an active treatment agent the improvement characterized by feeding to such water system an aqueous-based boron compound(s) composition including a signature chemical and optionally a water-soluble polypolar organic compound containing hydroxyl, primary amino, or secondary amino functional groups, and having a molecular weight not exceeding 500, preferably a (poly)ethanol amine, and employing the signature chemical as a tracer for the monitoring of the boron compound(s). The present invention also provides a process for inhibiting amorphous silica scale formation on surfaces in contact with the water of an aqueous system having a pH of at least 5 and containing dissolved silicates, wherein a boron compound(s) is employed as the functional silica scale deposit inhibitor, and is added to the aqueous system together with a signature chemical, and the boron compound(s) is monitoring through the signature chemical. The present invention and these and other preferred embodiments thereof are described in more detail below.

PREFERRED EMBODIMENTS OF THE INVENTION

As used herein, the terminologies of "boron compound(s)", boric acid or other boron compound(s)", and "boric acid or like boron compounds" means any one or a plurality, in combination, of the compounds of boric acid and its water-soluble salts, and/or any boron compound that forms orthoborate ion by dissolving in water or by hydrolysis under water environments. Boric acid is the preferred compound among such group of compounds, being most commonly employed commercially, and also generally being the most active compound, particularly for amorphous silica scale deposit inhibition.

The present invention in its broadest embodiments is not dependent upon the concentration of boric acid or other boron compound(s) when fed to the fluid system. Boric acid ($H_3BO_3$) is soluble in water only to a limited extent. Its water-solubility varies from about 2.66 parts by weight boric acid per hundred parts by weight water at 0° C. to about 40.2 parts by weight boric acid per hundred parts by weight water at 100° C. At ambient room temperature (from about 20° C. to about 26° C.) the solubility of boric acid in water is from about 4 to about 6 weight percent. The present invention includes a process wherein boric acid or other boron compound(s) is fed to a fluid system as a dilute aqueous solution, for instance one containing up to about 6 weight percent of the boron compound(s), as boric acid.

A liquid composition of boric acid or other boron compound(s) having a high concentration, particularly an aqueous-based composition, may provide a number of advantages in comparison to dilute solution or products in solid or dry form. A concentrated liquid composition can be supplied without the costs and energy consumption entailed in the shipping and/or handling and/or storage of a product that is either highly dilute or requires dissolution before use. A concentrated liquid composition can at times be fed directly to an industrial aqueous system by means of a fluid metering pump or other conventional fluid feed means, without either on-site mixing equipment or some degree of shipping and/or handling and/or storage of solution if prepared off-site. In addition, a concentrated liquid may be a particularly advantageous form for delivery of boric acid or other boron compound(s) as an active water-treatment agent to an aqueous system. The present invention includes a process wherein boric acid or other boron compound(s) is fed to a fluid system as a concentrated liquid, for instance as described in aforementioned U.S. Pat. No. 4,532,047, concomitantly with a signature chemical.

A simple high-concentration boric acid solution in water at ambient temperatures is of course precluded by the limited water-solubility of boric acid. Boric acid is known to be soluble to a greater degree in some organic solvents, for instance having a solubility on the order of about 15 to 20 weight percent at ambient room temperature. The present invention includes a process wherein the boric acid or other boron compound(s) is fed as a solution in an organic solvent or as a solution in a mixed solvent system, such as a solvent system comprised of water and one or more organic solvents, concomitantly with a signature chemical.

By feeding a signature chemical concomitantly with the boric acid or other boron compound(s) is meant herein that the feed of the boric acid or other boron compound(s) includes such signature chemical. It is believed that no other method of concomitant addition would sufficiently assure that the desired proportionality between the signature chemical and the boric acid or other boron compound(s) in the fluid system is achieved. For instance, if separate feeds of the signature chemical and the boric acid or other boron compound(s) were used, even though the concentrations of each in the respective feed compositions were known, the feed rates could not be assured to be the same. Moreover, one advantage of the present invention is to monitor the concentration of the signature chemical, and thus the boric acid or other boron compound(s), despite imprecise feed-rate determinations, and hence avoids the use of highly-sensitive feed-rate monitoring equipment.

The signature chemical, also referred to herein as a tracer or tracer species, is in most all instances preferably an inert compound in the use environment, as discussed elsewhere herein.

Boric acid dissolves in water to form the orthoborate ion. As discussed in U.S. Pat. No. 4,584,104, the orthoborate ion apparently must be present for silica scale inhibition, and boron compounds that form orthoborate ion upon dissolution and/or hydrolysis in water are active for silica scale deposit inhibition. The water-soluble salts of boric acid form orthoborate ion in water, and they include, but are not limited to, sodium lithium, potassium, ammonium and quaternary ammonium salts and alkaline earth metal salts, aluminum salts and transition metal salts if the presence of these types of cations can be tolerated in the water system and if such cations are compatible with the chosen parameters within the process of the present invention. Other boron compounds that form orthoborate ion upon dissolution and/or hydrolysis in water include, but are not limited to, fluoroboric acid and sodium tetrahydridoborate. As mentioned above, boric acid itself is commercially the most common source of orthoborate ion, and boric acid is the most commonly used boron compound, but the present invention does not exclude the use of boric acid salts or other orthoborate ion forming boron compounds when such salts and other boron compounds are adequate for a given purpose. For simplicity, the present invention is frequently described below with reference to "boric acid or other boron compound(s)" wherein the "other boron compound(s)" includes those described above.

The signature chemical (at least one specie of chemical tracer) is fed to the fluid system in an admixture together with the boric acid or other boron compound(s), as is mentioned elsewhere herein. Such admixture preferably is a solution of the boric acid or other boron compound(s) and the signature chemical in a solvent for both, for instance an aqueous solution containing both boric acid or other boron compound(s) and the signature chemical as solutes. Such aqueous solution, or other admixture, may contain other components. For instance, an aqueous solution of boric acid or other boron compound(s) and the signature chemical may contain one or more of the water-soluble polypolar organic compounds described above, and in preferred embodiment does contain one or more of the water-soluble polypolar organic compounds, and in more preferred embodiment the one or more of the water-soluble polypolar organic compounds employed is monoethanol amine or triethanol amine. In more preferred embodiment the aqueous solution of boric acid or other boron compound(s) and the signature chemical contains one or more of such water-soluble polypolar organic compounds, particularly monoethanol amine or triethanol amine, in an amount effective to increase the solubility of boric acid or other boron compound(s) in such aqueous solution. In even more preferred embodiment the aqueous solution of boric acid or other boron compound(s) and the signature chemical contains one or more of such water-soluble polypolar organic compounds, particularly monoethanol amine or triethanol amine, in an amount of at least one part by weight for every six parts by weight of the boric acid or other boron compound(s) (as boric acid). In another preferred embodiment the aqueous solution of boric acid or other boron compound(s) and the signature chemical contains one or more of such water-soluble polypolar organic compounds, particularly monoethanol amine, in an amount of at least one part by weight for every six parts by weight of the boric acid or other boron compound(s) (as boric acid) up to about one part by weight for every one part by weight of the boric acid or other boron compound(s) (as boric acid). Neither monoethanol amine or triethanol amine are flammable, and their presence in the aqueous solution together with the boric acid or other boron compound(s) and the signature chemical will increase the water solubility of the boric acid or other boron compound(s). Aqueous solutions of boric acid or other boron compound(s) can be provided with concentrations of boric acid or other boron compound(s) (as boric acid) up to about 55 weight percent or possibily higher at ambient room temperature with the inclusion of monoethanol amine, for instance at a concentration of about 16 weight percent in the aqueous solution, and the further incorporation of a signature chemical as a solute is generally believed not harmful to the enhanced solubility of the boric acid or other boron compound(s) provided by the inclusion of one or more of such water-soluble polypolar organic compounds, particularly the mono-and/or triethanol amines.

The water-soluble polypolar organic compounds, as noted above, generally have molecular weights not exceeding 500, and preferably have molecular weights not exceeding 200. The polypolarity of these compounds may be derived from polyhydroxy substituents, as for instance in compounds such as ethylene glycol, glycerine, mannitol, sorbitol, tris-hydroxymethyl methane, tris-hydroxymethyl methanol and the like. The polypolarity of these compounds may be derived from polyamine substituents, as for instance in the compounds ethylene diamine, triethylene tetramine, 1,6-hexamethylene diamine, bis-hexamethylene triamine, tetraethylene pentamine and the like. The polypolarity of these compounds may also be derived from combinations of hydroxyl and amine substituents, which compounds include the monoethanol amine (2-aminoethanol) and triethanol amine (tri-(2-hydroxethyl)amine) mentioned above and other alkanol amines such as diethanol amine, N-ethylamino monoethanol amine, N,N, diethanol amine, N,N,N,N-tetrakis(hydroxy ethyl)ethylene diamine and the like.

The monoethanol amine or triethanol amine, or other species of the water-soluble polypolar organic compounds described above, or other component of the aqueous solution or other form of admixture, may be present in the aqueous solution or other form of admixture together with the boric acid or other boron compound(s) and the signature chemical as a treatment chemical (for instance a silica scale deposit inhibitor agent, a chelant, an organic or inorganic corrosion inhibition agent, a polymeric dispersant, a biocide and/or other agents or combinations of such agents), as a boric acid or other boron compound(s) solubility enhancing agent, or for other purposes and even for no particular purpose, provided that such other component does not have such a deleterious effect on either the boric acid or other boron compound(s) or the signature chemical so as to diminish the amount of such components to an amount below the minimum effective amount. An effective amount of the boric acid or other boron compound(s) is the amount necessary in the feed solution or other form of admixture to be effective in the fluid system for the purpose(s) for which it is being added to the fluid system, at the rate in which the feed is fed to the fluid system. An effective amount of the signature chemical is the amount necessary in the feed solution or other form of admixture to be effective in the fluid system for the purpose(s) for which it is being added to the fluid system, at the rate in which the feed is fed to the fluid system. Generally the signature chemical is being fed to the fluid system for the purposes of detecting at least the existence of signature chemical in a sample of fluid taken from the fluid system, as is described in more detail below.

The admixture of boric acid or other boron compound(s) and signature chemical may be other than an aqueous solution, for instance a mixed solvent system or an organic solvent solution, preferably provided that both the boric acid or other boron compound(s) and signature chemical are soluble therein at practical concentrations, particularly at ambient room temperature. The organic solvent of such a mixed solvent system (water and organic solvent system) or such an organic solvent solution in preferred embodiment is one or more of the water-soluble polypolar organic compounds having a molecular weight not exceeding 500, and more preferably not exceeding 200, which are described and discussed above. Thus an aqueous solution containing boric acid or other boron compound(s), water and one or more of the water-soluble polypolar organic compounds is inherently also a mixed solvent system. As examples of substantially wholly organic solvent solutions employing one or more of the water-soluble polypolar organic compounds are solutions of boric acid or other boron compound(s), and at least one specie of chemical tracer, in glycol, glycerine, glycol/glycerine mixtures, diethylene glycol and the like. As examples of mixed solvent solutions employing one or more of the water-soluble polypolar organic compounds are solutions of boric acid or other boron compound(s) in glycol/water mixtures, glycerine/water mixtures, glycol/glycerine/water mixtures, monoethanol amine/water mixtures, triethanol amine/water mixtures and the like mixtures.

As a feed to a fluid system, most solutions containing the boric acid or other boron compound(s) and signature chemical would be at ambient room temperature at the time of such feeding, but the present invention of course does not exclude the selection of other concentrations of boric acid or other boron compound(s) and/or signature chemical that may be possible and/or practical for feed at other than ambient room temperature, for instance at elevated temperatures, at which boric acid or other boron compound(s) would generally be more soluble in at least water, and at lower than ambient room temperature.

The admixture of boric acid or other boron compound(s) and signature chemical may be other than a solution, for instance it may be a solid or dry form admixture or a colloid form admixture or any other type of admixture, provided there is a sufficiently homogeneous, or consistent, distribution of the boric acid or other boron compound(s) and signature chemical in such admixture to release into the fluid system by such common feed related concentrations of boric acid or other boron compound(s) and signature chemical. In more detail, at minimum for the purposes of the present invention, the detection of the presence of the signature chemical in a sample taken from the fluid system should be indicative of the presence of boric acid or other boron compound(s) in that sample also. In more preferred embodiment, an analysis of a sample taken from the fluid system will indicate the concentration of the signature chemical in the fluid system at the sampling point, and that in turn preferably should indicate at least approximately the concentration of the boric acid or other boron compound(s) in the fluid system at the sampling point. The determination or calculation of the boric acid or other boron compound(s) concentration from the signature chemical concentration generally requires that at least the relative amounts of boric acid or other boron compound(s) and signature chemical fed to the fluid system at a given time be known. For fluid systems that are comprised of, or include, flowing streams, for instance an industrial cooling water system, an admixture of boric acid or other boron compound(s) and signature chemical must be relatively homogeneous as fed to reasonably assure that any subsequent downstream analysis of signature chemical can be reasonably related to boric acid or other boron compound(s), and such homogeneous admixture is generally ensured for a true solution, but might not be achieved in a dry admixture, for instance, unless particular care is taken in the formulation and/or compounding thereof. For a more static fluid system such a high degree of homogenization may not be necessary, for instance when the admixture is fed to a fluid system that will permit dissolution of the boric acid or other boron compound(s) and signature chemical into the fluid thereof prior to any substantial translation of the fluid.

In a preferred embodiment, the fluid system is substantially an aqueous system, or at least a fluid system containing at least about 40, or 50 weight percent water, and the boric acid or other boron compound(s) and signature chemical are fed to such fluid system as an aqueous solution or organic solvent solution or mixed solvent solution. In more preferred embodiment, scuh solution or feed contnains from about 0.5, or 1, to about 55, or 60, weight percent boric acid or other boron compound(s), and in even more preferred embodiment at least about 10, or 15, to about 55, or 60, weight percent boric acid or other boron compound(s). In another more preferred embodiment, such solution or feed is a mixed solvent solution which contains from about 0.5, or 1, to about 25, or 30, weight percent water-soluble polypolar organic compound as described above, and in even more preferred embodiment at least about 10, or 15, to about 25, or 30, weight percent water-soluble polypolar organic compound as described above, particularly when such water-soluble polypolar organic compound is triethanol amine or monoethanol amine. In another more preferred embodiment, the mixed solvent solution or feed contains from about 0.5, or 1, to about 55, or 60, weight percent boric acid or other boron compound(s) and from about 0.5, or 1, to about 25, or 30, weight percent water-soluble polypolar organic compound as described above, and in even more preferred embodiment at least about 10, or 15, to about 55, or 60, weight percent boric acid or other boron compound(s) and at least about 10, or 15, to about 25, or 30, weight percent water-soluble polypolar organic compound as described above, particularly when such water-soluble polypolar organic compound is triethanol amine or monoethanol amine.

The preferred concentration of signature chemical in such aqueous or mixed solvent solution or feed is described below in more detail in terms of concentration thereof in the fluid system after the signature chemical feed is added. Generally, the concentration of signature chemical would not exceed that of the boric acid or other boron compound(s) in a feed solution, and since there is no practical purpose for the addition of signature chemical in amounts greater than that required to provide an effective amount of the signature chemical in the fluid system, in preferred embodiment the amount of signature chemical is no more than about 1 part by weight of the signature chemical per 10 parts by weight of boric acid or other boron compound(s) (as boric acid).

When the feed composition also contains one or more of the water-soluble polypolar organic compounds for at least in part the purpose of adding such water-soluble polypolar organic compound as itself as an amorphous silica scale deposit inhibitor, such feed preferably should contain a sufficient concentration of the water-soluble polypolar organic compound to provide in the fluid system an effective amount thereof for such inhibition purpose, and an effective amount of the water-soluble polypolar organic compound in the fluid system is often at least about 10 ppm when the fluid system is comprised of industrial waters, and may be at least about 50 or 100 ppm, in each instance based on parts by weight of the water-soluble polypolar organic compound per million parts by weight of the industrial waters.

In a preferred embodiment, the fluid system is an industrial water system, particularly industrial water systems such as: heat-exchange systems, including, but not limited to, cooling water systems; geothermal water systems; salt water systems for desalinization purposes; industrial systems containing waters being prepared for boiler treatment and steam generation; downhole water systems for petroleum crude recovery; reverse osmosis systems; and the like. Such industrial water systems often have significant amorphous silica scale deposit problems, and employ boric acid or other boron compound(s) as an inhibitor thereof, and hence the process of the present invention is highly advantageous for use in monitoring the boric acid or other boron compound(s) in such waters. In such industrial water systems boric acid or other boron compound(s) may be added to the system as an amorphous silica scale deposit inhibitor or as a component of a multi-component amorphous silica scale deposit inhibition program or instead for other purposes. When the boric acid or other boron compound(s), or when the water-soluble polypolar organic compound described above, are employed as amorphous silica scale deposit inhibitor(s) or as a component(s) of a multi-component amorphous silica scale deposit inhibition program, the waters commonly have a neutral to alkaline pH, for instance a pH value of at least about 5 and commonly higher than 6, and contain at least 5 ppm dissolved silica as $SiO_2$, and at times as high as 350 or 450 ppm, or even up to 1,000 ppm, dissolved silica as $SiO_2$ or more. The condensation of silicic acid to amorphous silica is driven by alkalinity, and thus waters of higher alkalinity will have a greater tendency towards amorphous silica scale formation for a given concentration of dissolved silica, other factors being constant. Such waters may also contain, in addition to dissolved silica, silica in dispersed or even colloidal forms. In addition the calcium hardness of the water, which commonly is at least as high as 50 ppm as $CaCO_3$ and routinely is much higher, such as up to 1,000 ppm as $CaCO_3$ or more, aggravates the silica scale deposit potential. Such water conditions routinely are found in industrial systems with silica scale deposit problems.

The temperatures encountered within a fluid system are of course dependent upon the type of fluid system. Industrial water systems commonly vary in temperature from about ambient room temperature up to about 150° C., and at times higher than 150° C. For instance industrial geothermal water can exceed 250° C. or 260° C., and boric acid or other boron compound(s), alone or together with one or more of the water-soluble polypolar organic compounds described above, may be added to such high temperature water for amorphous silica scale deposit inhibition purposes or other purposes.

It is common to treat the waters of industrial cooling water systems with boric acid or other boron compound(s), alone or together with one or more of the water-soluble polypolar organic compounds described above. Such cooling waters are routinely neutral to alkaline as described above and may require boric acid or other boron compound(s) addition even if the cooling waters are employed in the cooling water system on a once-through basis. Addition of boric acid or other boron compound(s) is however even more frequently required, and an efficient process for monitoring of the added boric acid or other boron compound(s) is more seriously needed, when the cooling waters are within a recirculating cooling water system. Within a recirculating cooling water system the impurities in the make-up waters routinely become concentrated by up to a factor of 10 or more, and such concentration exaggerates water problems, such as silica scale deposits. A reasonably low concentration of a solute, such as silica, in the make-up water becomes seriously high as such water becomes more and more concentrated. The alkalinity of the waters also frequently increases with such concentration, and pH values of about 7 or 9 or higher are frequently encountered in concentrated cooling waters of recirculating cooling water systems.

As noted above, the boric acid or other boron compound(s) composition as fed to a fluid system, particularly an industrial water system, may further contain other components, which may be active components in the fluid system or may be inert components in the fluid system. Such other materials may be fed to the fluid system separately from the boric acid or other boron compound(s) composition feed. Among such other materials that are commonly added to industrial water systems are those used to inhibit corrosion or to disperse or inhibit scale formation of types other than amorphous silica scale, such inhibitors including chromium, zinc, phosphates, orthophosphates, polyphosphates, low molecular weight (commonly under 500,000 daltons) polymers of acrylic acid, acrylamide, and various acrylates which are primarily used as threshold agents or dispersants in fluid systems such as cooling water systems.

The signature chemical(s) is herein at times referred to as a "tracer", the functional "tracer" terminology being applicable to the signature chemical(s) because it acts as a tracer for the purposes of the present invention. The tracer is preferably selected from among those that are easily detectable by the analysis method being employed in a given application of the present process. Such analysis methods include, but are not limited to, fluorescence analysis, colorimetry analysis, transition metal analysis, and combinations of high pressure liquid chromatography ("HPLC") and these or other detection method such as light absorbance analysis, post-column derivitization, conductivity and the like, some of which are described in more detail below.

Fluorescence Emission Spectroscopy

The detection and quantification of specific substances by fluorescence emission spectroscopy is founded upon the proportionality between the amount of emitted light and the amount of a fluoresced substance present. When energy in the form of light, including ultra violet and visible light, is directed into a sample cell, fluorescent substances therein will absorb the energy and then emit that energy as light having a longer wavelength than the absorbed light. The amount of emitted light is determined by a photodetector. In practice, the light is directed into the sample cell through an optical light filter or monochromator so that the light transmitted is of a known wavelength, which is referred to as the excitation wavelength and generally reported in nanometers ("nm"). The emitted light is similarly screened through a filter so that the amount of emitted light is measured at a known wavelength or a spectrum of wavelengths, which is referred to as the emission wavelength and generally also reported in nanometers. When the measurement of specific substances or categories of substances at low concentrations is desired or required, such as often is the case for the process of the present invention, the filters are set for a specific combination of excitation and emission wavelengths, selected for substantially optimum low-level measurements.

Fluorescence emission spectroscopy is one of the preferred analysis techniques for the process of the present invention. Certain compounds are inherently fluorescent or may be tagged to provide a traceable fluorescent characteristic. As noted elsewhere, the tracer used in the present invention is preferably an inert chemical, not substantially consumed in the use environment. The tracer should also preferably be soluble in the fluid of the fluid system, and since the fluid system in certain preferred embodiments is an aqueous system, in such preferred embodiments the tracer should be water-soluble at least at the concentration of the tracer that is employed in the aqueous system. Many types of water-soluble fluorescent chemicals which are substantially inert in most aqueous environments are known. Among these substantially inert fluorescent compounds are the mono-, di- and trisulfonated naphthalenes, such as the various naphthalene disulfonic acid isomers, which are preferred signature chemicals for use in the present invention. The naphthalene disulfonic acid isomers are water-soluble, generally available commercially and easily detectable and quantifiable by known fluorescence analysis techniques. Moreover, such signature chemicals have been found to be compatible with at least some of the mixed solvent solutions of boric acid or other boron compound(s) described above, and so can be easily incorporated into the feed of boric acid or other boron compound(s) to the aqueous system.

Some naturally fluorescent compounds are also water treatment agents, and thus may be among the normal compounds added to an aqueous system such as cooling waters, for instance aromatic organic corrosion inhibitors, such as aromatic(thio)(tri)azoles. Some water treatment agents may be susceptible to tagging with fluorescent groups, for instance as disclosed in U.S. Pat. No. 5,128,419, D. W. Fong and J. E. Hoots, issued Jul. 7, 1992, incorporated herein by reference, wherein the tagging of polymers with pendant fluorescent groups by (trans)amidation derivatization of pre-existing polymers having carbonyl-type pendant groups is disclosed. Water-treatment polymers tagged with pendant fluorescent groups may of course be prepared by methods other than (trans)amidation derivatization. Other fluorescent chemical tracers and monitoring techniques are now known, for instance as disclosed in U.S. Pat. No. 4,783,314, J. E. Hoots and B. E. Hunt, issued Nov. 8, 1988, incorporated herein by reference, wherein inert fluorescent tracers are employed in combination with a fluorescence monitoring, such as the sodium salt of 2-naphthalenesulfonic acid and Acid Yellow dye. Such naturally fluorescent or fluorescence-tagged water-treatment compounds are useful for the purposes of the present invention only when they can provide the monitoring desired by the present invention despite their potential for consumption to some degree in the performance of their water-treatment functionality(ies), and in preferred embodiment the use of fluorescent water-treatment species, or other water-treatment species, as the tracer in the present process is excluded.

In general for most fluorescence emission spectroscopy methods having a high degree of practicality, it is preferable to perform the analysis without isolating in any manner the fluorescent tracer. Thus there may be some degree of background fluorescence. In instances where the background fluorescence is low, the relative intensities (measured against a standard fluorescent compound at a standard concentration and assigned a relative intensity for instance 100) of the fluorescence of the tracer versus the background can be very high, for instance a ratio of 100/10 or 500/10 when certain combinations of excitation and emission wavelengths are employed even at low fluorescent compound concentrations, and such ratios would be representative of relative performance (under like conditions) of respectively 10 and 50. For most cooling water backgrounds, a compound that has a relative performance of at least about 5 at a reasonable concentration is very suitable as a fluorescent tracer itself or as a tagging agent for water treatment polymers and the like when such compounds contain an appropriate reactive group for the tagging reaction. When there is or may be a specific chemical species of reasonably high fluorescence in the background, the tracer and the excitation and/or emission wavelengths often can be selected to nullify or at least minimize any interference of the tracer measurement(s) caused by the presence of such species.

One method for the continuous on-stream monitoring of chemical tracers by fluorescence emission spectroscopy and other analysis methods is described in U.S. Pat. No. 4,992,380, B. E. Moriarity, J. J. Hickey, W. H. Hoy, J. E. Hoots and D. A. Johnson, issued Feb. 12, 1991, incorporated hereinto by reference.

Combined HPLC-Fluorescence Analysis

The combination of high-pressure liquid chromatography ("HPLC") and fluorescence analyses of fluorescent tracers is a powerful tool for the present boric acid or other boron compound(s) monitoring process, particularly when very low levels of the fluorescent tracer are used or the background fluorescence encountered would otherwise interfere with the efficacy of the fluorescence analysis. The HPLC-fluorescence analysis method allows the tracer compound to be separated from the fluid matrix and then the tracer concentration can be measured. The combination of HPLC-fluorescence analysis is particularly effective for measuring minute levels of tracer in highly contaminated fluids.

The HPLC method can also be effectively employed to separate a tracer compound from a fluid matrix for the purposes of then employing a tracer-detection method other than fluorescence analysis, and such other tracer-detection methods include, without limitation, light absorbance, post-column derivatization, conductivity and the like.

Colorimetry Analysis

Colorimetry or spectrophotometry may be employed to detect and/or quantify a chemical tracer. Colorimetry is a determination of a chemical species from its ability to absorb ultraviolet or visible light. One colorimetric analysis technique is a visual comparison of a blank or standard solution (containing a known concentration of the tracer species) with that of a sample of the fluid being monitored. Another colorimetric method is the spectrophotometric method wherein the ratio of the intensities of the incident and the transmitted beams of light are measured at a specified wavelength by means of a detector such as a photocell or photomultiplier tube. Using a colorimetric probe, a fiber optic (dual) probe, such as a Brinkman PC-80 probe (570 nm filter), a sample solution is admitted to a flowcell in which the probe is immersed. One fiber optic cable shines incident light through the sample liquid onto a mirror inside the cell and reflected light is transmitted back through the sample liquid into a fiber optic cable and then to the colorimetric analyzer unit, which contains a colorimeter, by the other cable. The colorimeter has a transducer that develops an electrical analog signal of the reflected light characteristic of the tracer concentration. The voltage emitted by the transducer activates a dial indicator and a continuous line recorder printout unit. A set point voltage monitor may be employed to constantly sense or monitor the voltage analog generated by the colorimeter, and upon detection of a tracer signal (discussed below), a responsive signal may be transmitted to a responsive treatment agent feed line to commence or alter the rate of feed. Such a colorimetric analysis technique and the equipment that may be employed therefor are described in U.S. Pat. No. 4,992,380, B. E. Moriarity, J. J. Hickey, W. H. Hoy, J. E. Hoots and D. A. Johnson, issued Feb. 12, 1991, incorporated hereinto by reference. Chemical tracers suitable for use in conjunction with a colorimetric technique include transition metals (discussed below) and substances which show light absorbance which is detectable from that of other species present in the system fluid or substances which react with color-forming reagents to produce light absorbance which is detectable from that of other species present in the system fluid.

Transition Metal Analysis

A transition metal compound (transition metal ions, oxy-anions, cations and associated complexes) can be quantitatively measured by one or more of known techniques. A preferred technique is the colorimetry analysis discussed above. Another technique is molecular absorption. Molecular absorption in the ultra violet and visible regions on the electronic structure of the molecule. The energy absorbed elevates electrons from orbitals in a lower-energy state to orbitals in a higher-energy state. A given molecule can absorb only certain frequencies because only certain states are possible in any molecule and the energy difference between any ground and excited state must be equal to the energy added. At a frequency that is absorbed by a molecule, the intensity of the incident energy is greater than the intensity of the emergent energy, and is a measure of the absorbance. A sample of the fluid being monitored may be compared to a calibration curve (absorbance versus concentration) prepared from standard solutions containing known concentrations of the transition metal (or other suitable tracer species) to detect and determine the concentration of the tracer. A molecular absorption technique for transition metal tracers is described in U.S. Pat. No. 4,992,380, B. E. Moriarity, J. J. Hickey, W. H. Hoy, J. E. Hoots and D. A. Johnson, issued Feb. 12, 1991, incorporated hereinto by reference.

Analytical techniques for detecting the presence and/or concentration of a chemical species without isolation thereof are within an evolving technology, and the above survey of reasonable analytical techniques for use in the process of the present invention may presently not even be exhaustive, and most likely techniques equivalent to the above for the purposes of the present invention will be developed in the future.

A chemical species may be selected for a given process based on a preference for one or more analytical techniques, or an analytical technique may be selected for a given process based on a preference for one or more chemical tracers. In preferred embodiments, the chemical compound(s) selected as the tracer should be soluble in the fluid of the process, at least at the concentration level(s) of the chemical tracer employed in the respective fluid. In one preferred embodiment, the chemical compound(s) selected as a tracer should be either stable in the environment of the fluid system for the useful life expected of the tracer, or its loss from the fluid due to degradation, deposition, complexation, or other phenomena should be predictable and compensative, particularly when it is desired not merely to detect the presence of some amount of the tracer, but also to determine the concentration thereof, or change in concentration.

In another preferred embodiment, the chemical compound(s) selected as a tracer should not be one that is consumed or lost to the fluid, for instance due to degradation, deposition, complexation, or other phenomena, unless such consumption or loss is at a rate that is predictable and proportional to the loss of the boric acid or other boron compound(s) to the fluid, particularly when it is desired to determine the concentration, or change in concentration, of the boric acid or other boron compound(s) in the fluid. When boric acid or other boron compound(s) is used for amorphous silica scale deposition inhibition, it is believed that the boric acid or other boron compound(s) has a negligible consumption or loss rate in an aqueous system.

In preferred embodiment, the combination of the chemical compound(s) selected as the tracer and the analytical technique selected for determining the presence and/or concentration of such tracer, should permit such determination(s) without isolation of the tracer, and more preferably should permit such determination(s) on a continuous and/or on-line basis.

In another preferred embodiment, the analytical technique(s) selected for determining the presence and/or concentration of a tracer, should permit such determination(s) to provide a signal that can activate or regulate the feed of the boric acid or other boron compound(s) composition to the fluid being treated with, or for other purposes dosed with, the boric acid or other boron compound(s) composition.

One embodiment the process of the present invention is comprised of adding a chemical tracer to the boric acid or other boron compound(s) composition itself, before such composition is fed to the fluid system. In another embodiment of the present invention, the chemical tracer is added as a separate but concomitant feed to the fluid system together with the boric acid or other boron compound(s) composition feed. The present invention does not exclude a process comprised of adding a chemical tracer both to the boric acid or other boron compound(s) composition before it is fed to the fluid system, and directly to the fluid system as a separate but concomitant feed together with the boric acid or other boron compound(s) feed, but such dual-feed method is of much less value when the dual feed rates cannot conveniently be accurately determined.

More than one chemical tracer can be employed, and then the presence and/or concentration of each such tracer in the fluid system should be determined by an analytical technique effective for each such tracer, which analytical techniques may be the same or different.

In further preferred embodiments, when the fluid system has more than one potential boric acid or other boron compound(s) routes, such as in a series of connected systems having multiple product feed points, the aforesaid sampling and analyses are conducted at more than one site, particularly at at least one site along at least a plurality of routes, and more preferably substantially at at least one site along each of such potential boric acid or other boron compound(s) routes. By monitoring at at least one site along separate potential boric acid or other boron compound(s) routes, the location(s) of the boric acid or other boron compound(s) among such routes can be determined, and the extent of boric acid or other boron compound(s) flow to the separate routes may also be determined.

EXAMPLE 1

A stable mixed solvent solution of boric acid with a naphthalene disulfonic acid tracer was prepared by admixing the following components:

28 parts by weight water
17 parts by weight monoethanol amine
55 parts by weight boric acid
0.26 parts by weight naphthalene disulfonic acid

EXAMPLE 2

A stable mixed solvent solution of boric acid with a vanadium tracer was prepared by admixing the following components:

46.2 parts by weight water
34 parts by weight monoethanol amine
110 parts by weight boric acid
9.8 parts by weight of an aqueous solution containing 5.1 wt. percent vanadium In certain embodiments of the invention, the process includes the preliminary step of sampling the fluid system to determine baseline conditions, preferably at all intended or possible post-tracer-addition sampling sites. Such preliminary baseline condition(s) determination(s) may also be employed to narrow the selection choice of tracer chemicals or determine and/or modify the selection of post-tracer-addition sampling points.

In certain preferred embodiments, the sampling points are at the site(s) where the greatest mixing of the boric acid or other boron compound(s) with the waters to be treated has occurred. If the greatest concern is the presence and/or concentration of boric acid or other boron compounds along one of a plurality of potential boric acid or other boron compounds routes, it is of course feasible to monitor only the route of concern. At times it may be most efficient to monitor the route that is most sensitive to both the detection and quantification of the tracer chemical, which sensitivity may be derived from the baseline condition(s) of such route or the concentration of tracer chemical expected along such route. Monitoring the most sensitive route or the route of most concern in a given industrial installation may not, however, be the most practical. For instance, the fluid line(s) of such route(s) may be less accessible to monitoring than other fluid lines. The fluid lines of the most sensitive route and/or the route of most concern may be susceptible to monitoring only by a less desirable analytical method. Thus while the monitoring of the fluid within the route of most concern or the route most sensitive to monitoring is desirable, circumstances can render that approach less desirable for practical reasons.

Generally it is desirable to employ the least amount of tracer chemical that is practical for the circumstance, and the amount of the tracer added to the fluid system should be at least an amount effective for the determinations desired. Seldom would a tracer be deliberately fed to a fluid system in an amount grossly in excess of the minimum effective amount because there generally would be no practical purpose in doing so that would justify the costs involved and any deleterious effects on the quality of either of the fluids caused by the presence of the tracer chemical therein. The amount of tracer chemical to be added to the tracer-receiving fluid system that is effective without being grossly excessive will vary with a wide variety of factors, including without limitation the tracer and monitoring method selected, the potential for background interference with the selected monitoring method, the magnitude of the suspected or potential leakage, the monitoring mode (on-line continuous, semi-continuous, slug-and-sample, and the like). Generally the dosage of tracer to the fluid system will be at least sufficient to provide a concentration of tracer therein of about 0.1 ppm, and more commonly at least about 10 or 100 ppm or higher.

The present invention in an embodiment is a process for monitoring boric acid or other boron compounds in a fluid system, comprising: adding boric acid or other boron compounds to the fluid system; adding to the fluid system at least one specie of tracer chemical; and subjecting at least one sample of fluid from at least one site of the fluid system to at least one analysis; wherein the analysis at least detects the presence of the specie of tracer chemical in the sample, and wherein the analysis at least determines the presence of boric acid or other boron compounds in the sample by the detection of the presence of the specie of tracer chemical.

The present invention in an embodiment is a process for monitoring boric acid or other boron compounds in a fluid system, comprising: adding to the fluid system a composition comprised of an admixture containing boric acid or other boron compounds and at least one specie of tracer chemical, wherein the proportion of the specie of tracer chemical to the boric acid or other boron compounds in the admixture is substantially known; subjecting at least one sample of fluid from at least one site of the fluid system to at least one analysis; and wherein the analysis at least detects the presence of the specie of tracer chemical in the sample, and wherein the analysis at least determines the presence of boric acid or other boron compounds in the sample by the detection of the presence of the specie of tracer chemical.

The present invention in an embodiment is a process for inhibiting amorphous silica scale formation on surfaces in contact with the water of an aqueous system having a pH of at least 5 and containing dissolved silicates comprising: adding to the water at least one boron compound that forms orthoborate ion when dissolved or hydrolyzed by the water in an amount effective for inhibiting the formation of amorphous silica scale on surfaces in contact with the water; adding at least one specie of tracer chemical to the water concomitantly with the addition of the boron compound; and monitoring the boron compound in the aqueous system by determining at least one site of the aqueous system at least the presence of the specie of tracer chemical.

In preferred embodiments, the analysis determines a spectral or chemical characteristic of the specie of chemical tracer that is proportional to the concentration of the specie of chemical tracer in the fluid system analyzed. The specie of chemical tracer in some preferred embodiments is a transition metal cation that is at least in part the cation of a water-soluble boron salt and the analysis is a transition metal-responsive analysis.

The specie of chemical tracer in another preferred embodiment is at least one fluorescent compound and the analysis at least includes fluorescence analysis and preferably is an on-line continuous or semi-continuous analysis. The boric acid or other boron compounds and the specie of chemical tracer are preferably substantially added together to the fluid system as a substantially aqueous or mixed solvent solution. Preferably at least a detection of the specie of chemical tracer activates or modifies a signal, and the signal upon activation or modification activates or modifies a feed of at least one treatment chemical to the fluid system.

In another preferred embodiment the admixture is a mixed solvent solution containing water and at least one water-soluble polypolar organic compound having a molecular weight not exceeding 500. In other preferred embodiments, the admixture is a mixed solvent solution containing water and at least one of monoethanol amine and triethanol amine. The boron compound is, in preferred embodiment, added to the water in an amount to provide a concentration of at least about 25 ppm as boric acid or other boron compounds as boric acid in the water. The specie of chemical tracer and the boron compound are, in preferred embodiment, added to the water of the aqueous system together as an admixture. The specie of chemical tracer and the boron compound are, in preferred embodiment, added to the water of the aqueous system together as a substantially aqueous solution. The specie of chemical tracer and the boron compound are, in other preferred embodiment, added to the water of the aqueous system together as a mixed solvent system containing water and at least one water-soluble polypolar organic compound having a molecular weight not exceeding 200. The aqueous system is preferably a heat-exchange water system, such as a cooling water system.

In certain preferred embodiments, the specie of chemical tracer is foreign to the normal treatment program for the fluid system, for instance when an inert tracer is added for the purposes of present invention, or both for the purposes of the present invention and for the purposes of a separate tracer process. In certain preferred embodiments, the specie of chemical tracer is at least one fluorescent compound and the analysis at least includes fluorescence analysis, which is particularly preferred because of the ease at which such method can be used for on-line continuous or semi-continuous monitoring, and other known advantages.

In certain preferred embodiments, the analysis is an on-line continuous or semi-continuous analysis of the fluid system, wherein at least a detection of the specie of chemical tracer activates or modifies a signal, and the signal upon activation or modification activates or modifies a feed of at least one treatment chemical to the fluid system, wherein the treatment chemical feed may be, and at times preferably is, a feed of the boric acid or other boron compounds composition to the fluid system.

In certain preferred embodiments, the analysis is an on-line continuous or semi-continuous fluorescence analysis of the fluid system and the specie of chemical tracer is at least one fluorescent compound, preferably a compound that is substantially inert in the fluid system. In certain preferred embodiments, the analysis is an on-line continuous fluorescence analysis of the fluid system and the specie of chemical tracer is at least one fluorescent compound, wherein at least a detection of the specie of chemical tracer activates or modifies a signal, and the signal upon activation or modification activates or modifies a feed of at least one treatment chemical to the fluid system, wherein the treatment chemical feed may be, and at times preferably is, a feed of a composition that contains boric acid or other boron compounds to the fluid system.

In certain preferred embodiments, the fluid system a heat-exchange system, and more preferably is a cooling water system.

In certain preferred embodiments, the fluid system is an aqueous stream that flows through a side of one or a plurality of heat-exchangers, including but not limited to cooling water streams.

In certain preferred embodiments, the analysis determines a spectral or chemical characteristic of the specie of chemical tracer that is proportional to the concentration of the specie of chemical tracer in the fluid system analyzed, and more preferably that is proportional to the concentrations of both the specie of chemical tracer and the boric acid or other boron compounds in the fluid system analyzed.

In certain preferred embodiments, the analysis is one or more of fluorescence emission spectroscopy, a combined high pressure liquid chromatography and fluorescence emission spectroscopy, a colorimetry spectrophotometry and a transition metal analysis. In certain preferred embodiments, the specie of chemical tracer is substantially resistant to depletion mechanisms in the environment of the fluids, such as degradation, deposition, consumption and other like depletion mechanisms. In certain embodiments, the specie of chemicaL tracer is substantially susceptible to depletion mechanisms in the environments of the fluid system in a degree or at a rate that is in proportion to the susceptibility of boric acid or other boron compounds to depletion mechanisms in the same environments.

Unless expressly indicated otherwise herein, all properties of any chemical compounds, or compositions containing a plurality of chemical compounds, set forth herein are such properties as would be determined for such compounds, or compositions, within a temperature range of from about 20° C. to about 40° C., and substantially under atmospheric pressure. By amorphous silica scale deposits is meant herein solid material that precipitates, or can be filtered, from an aqueous system and contains at least about 30 weight percent total silica as $SiO_2$ and more commonly contains from about 50 to 90 or more weight percent total silica as $SiO_2$, based on the total weight of dry material. By deposits is meant herein material that forms and/or collects on surfaces in contact with a fluid system. By the terminology "detection of the presence of" a chemical specie(s) is meant herein the determination of whether or not such chemical specie(s) is present or absent, and thus includes the detection of the absence of such chemical specie(s), at least to the limitations of the analytical method employed. By the terminology "as boric acid" following a mention of boron compound(s) other than boric acid is meant an amount of such boron compound(s) that would be equivalent to the stated amount of boric acid as to the orthoborate ion formed therefrom. Unless expressly indicated otherwise herein, the inclusion of a prefix or suffix in parenthesis designates the word with such prefix or suffix as an alternative. For instance, "compound(s)" means "compound and/or compounds", "determination(s)" means "determination and/or determinations", "technique(s)" means "technique and/or techniques", "location(s)" means "location and/or locations", "chemical(s)" means "chemical and/or chemicals", "inhibitor(s)" means "inhibitor and/or inhibitors", "component(s)" means "component and/or components", "specie(s)" means "specie and/or species", "functionality(ies)" means "functionality and/or functionalities", "aromatic(thio)(tri)azoles" means aromatic azoles and/or aromatic thiazoles and/or aromatic triazoles", and the like. The term "species" is at times used herein in reference to a single compound, as is apparent from the text concerning such references. The terminology "at least on specie of chemical tracer" means one or more chemical compounds that are within the chemical tracer, or tracer, category.

Industrial Applicability of the Invention

The present invention is applicable to all industries employing a fluid system that contains boric acid or other boron compounds, either as a chemical treatment additive, for instance as a silica scale deposit inhibition agent for cooling water systems, or for other purposes, particularly when it is desired to monitor the presence and/or concentration of boric acid or other boron compounds in such fluid system or any part thereof.

I claim:

1. A process for monitoring a boron compound that forms orthoborate ion in a fluid system, comprising:
    adding said boron compound to said fluid system;
    adding to said fluid system at least one specie of tracer chemical; and
    subjecting at least one sample of fluid from at least one site of said fluid system to at least one analysis;
    wherein said analysis at least detects the presence of said specie of tracer chemical in said sample,
    wherein said boron compound and said specie of chemical tracer are substantially added together to said fluid system as a substantially homogeneous stable aqueous or mixed solvent solution comprising a boron compound feed and containing no more than about 1 part by weight of said specie of chemical tracer per 10 parts by weight of said boron compound, and
    wherein said analysis at least determines the presence of said boron compound feed in said sample by said detection of the presence of said specie of tracer chemical.

2. The process of claim 1 wherein said specie of chemical tracer is substantially inert in the environment of said fluid system, and
    wherein said fluid system comprises at least about 40 weight percent water.

3. The process of claim 1 wherein said analysis senses a spectral or chemical characteristic of said specie of chemical tracer that is proportional to the concentration of said specie of chemical tracer in the fluid system analyzed,
    wherein said boron compound and said specie of chemical tracer are added together to said fluid system in known proportion, and
    wherein said analysis is correlated to the rate at which said boron compound being fed to the route along which said site at which said sample is taken is located.

4. The process of claim 1 wherein said specie of chemical tracer is a transition metal cation that is at least in part the cation of a water-soluble boron salt and said analysis is a transition metal-responsive analysis.

5. The process of claim 1 wherein said specie of chemical tracer is at least one fluorescent compound and said analysis at least includes fluorescence and is an on-line continuous or semi-continuous analysis.

6. The process of claim 1 wherein at least a detection of said specie of chemical tracer activates or modifies a signal, and said signal upon activation or modification activates or modifies a feed of at least one treatment chemical to said fluid system.

7. The process of claim 1 wherein said admixture is a mixed solvent solution containing water and at least one water-soluble polypolar organic compound having a molecular weight not exceeding 500, and
    wherein said admixture contains from about 10 to about 60 weight percent of said boron compound and from about 10 to about 30 weight percent of said water-soluble polypolar organic compound.

8. The process of claim 1 wherein said boron compound and said specie of chemical tracer are substantially added together to said fluid system as a substantially homogeneous stable mixed solvent solution comprising a solution in a glycol/water mixture, glycerine/water mixture, or glycol/glycerine/water mixture.

9. The process of claim 1 wherein said analysis senses a spectral or chemical characteristic of said specie of chemical tracer that is proportional to the concentration of said specie of chemical tracer in the fluid system analyzed,
    wherein said boron compound and said specie of chemical tracer are added together to said fluid system in known proportion,
    wherein said analysis is correlated to rate at which said boron compound being fed to the route along which said site at which said sample is taken is located, and
    wherein correlation activates or modifies a signal, and said signal upon activation or modification activates or modifies the rate at which said boron compound is added to said fluid system.

10. A process for monitoring a boron compound that forms orthoborate ion in a fluid system, comprising:
    adding to said fluid system a composition comprised of a substantially homogeneous stable admixture containing said boron compound and at least one specie of tracer chemical, wherein the proportion of said specie of tracer chemical to said boron compound in said admixture is substantially known;
    subjecting at least one sample of fluid from at least one site of said fluid system to at least one analysis; and
    wherein said analysis at least detects the presence of said specie of tracer chemical in said sample, and wherein said analysis at least determines the presence of said boron compound in said sample by said detection of the presence of said specie of tracer chemical, and wherein said boron compound is boric acid.

11. The process of claim 10 wherein said admixture is a mixed solvent solution containing water and at least one water-soluble polypolar organic compound having a molecular weight not exceeding 500, and wherein said mixed solvent solution contains from about 10 to about 60 weight percent of said boric acid.

12. The process of claim 10 wherein said admixture is a mixed solvent solution containing water and at least one of monoethanol amine and triethanol amine wherein said monoethanol amine or triethanol amine is present in said admixture in an amount of from about one part by weight for every six parts by weight of said boric acid to about one part by weight for every one part by weight of said boric acid.

13. The process of claim 10 wherein said specie of chemical tracer is at least one fluorescent compound and said analysis at least includes fluorescence analysis.

14. The process of claim 10 wherein said analysis is an on-line continuous or semi-continuous analysis of the fluid system.

15. The process of claim 10 wherein said analysis senses a spectral or chemical characteristic of said specie of chemical tracer that is proportional to the concentration of said specie of chemical tracer in the fluid system analyzed.

16. The process of claim 10 wherein said admixture is a mixed solvent solution containing water and at least one water-soluble polypolar organic compound having a molecular weight not exceeding 500, and wherein said admixture contains from about 10 to about 60 weight percent of said boron compound and from about 10 to about 30 weight percent of said water-soluble polypolar organic compound.

17. A process for inhibiting amorphous silica scale formation on surfaces in contact with the water of an aqueous system containing dissolved silicates comprising:

adding to said water at least one boron compound that forms orthoborate ion when dissolved or hydrolyzed by said water in an amount effective for inhibiting the formation of amorphous silica scale on surfaces in contact with said water;

adding at least one specie of tracer chemical to said water concomitantly with the addition of said boron compound; and monitoring said boron compound in said aqueous system by determining at least one site of said aqueous system at least the presence of said specie of tracer chemical.

wherein said specie of chemical tracer and said boron compound are added to said water of said aqueous system together as solutes of a substantially homogeneous stable mixed solvent system containing water and at least one water-soluble polypolar organic compound having a molecular weight not exceeding 200, and wherein the proportion of said specie of chemical tracer and said boron compound in said mixed solvent system are known.

18. The process of claim 17 wherein said boron compound is added to said water in an amount to provide a concentration of at least about 25 ppm as boric acid in said water.

19. The process of claim 17 wherein said specie of chemical tracer and said boron compound are added to said water of said aqueous system together as solutes of a mixed solvent system containing water and at least one water-soluble polypolar organic compound having a molecular weight not exceeding 200, and wherein said mixed solvent system is added to said water of said aqueous system in an amount sufficient to provide a concentration of said polypolar organic compound of at least 50 parts by weight of said polypolar organic compound per million parts by weight of water in said aqueous system.

20. The process of claim 17 wherein said aqueous system is a cooling water system, geothermal water system, salt water system for desalinization purposes, industrial system containing waters being prepared for boiler treatment and steam generation, downhole water system for petroleum crude recovery or reverse osmosis system.

* * * * *